United States Patent [19]

Shima et al.

[11] 3,954,895

[45] May 4, 1976

[54] METHOD OF SEPARATING AND RECOVERING ALKENYLBENZENES AND UNREACTED ALKYLBENZENES FROM THE ALKENYLATION REACTION PRODUCT

[75] Inventors: Takeo Shima; Michiyuki Tokashiki; Kazumi Iwata, all of Iwakuni, Japan

[73] Assignee: Teijin Limited, Osaka, Japan

[22] Filed: May 27, 1975

[21] Appl. No.: 581,052

[52] U.S. Cl. ........................ 260/668 B; 260/668 F; 260/671 A
[51] Int. Cl.² ........................................... C07C 3/52
[58] Field of Search .......... 260/668 B, 668 R, 668 F

[56] References Cited
UNITED STATES PATENTS

| 3,766,288 | 10/1973 | Shima et al. .................... 260/668 B |
| 3,865,889 | 2/1975 | Mitchell .......................... 260/668 B |
| 3,904,702 | 9/1975 | Mitchell .......................... 260/668 B |

Primary Examiner—C. Davis
Attorney, Agent, or Firm—J. Edward Hess; Donald R. Johnson

[57] ABSTRACT

In the method wherein an alkenylation reaction product liquid obtained by the alkenylation reaction of an alkylbenzene and a $C_4 - C_5$ conjugated diene in the presence of alkali metal catalysts and containing unreacted alkylbenzene, alkali metal catalysts and organoalkalimetal compounds is conveyed to a distillation zone at which said alkenylation reaction product liquid is separated by distillation to recover an alkenylbenzene-containing fraction and an unreacted alkylbenzene-containing fraction, the improvement which comprises adjusting the total of the concentrations of said alkali metal catalysts and organoalkalimetal compounds in said alkenylation reaction product liquid introduced to the distillation zone so as to be 0.09 – 15 milligram atoms per kilogram of said product liquid, calculated as alkalimetal atoms, and thereafter conducting the distillation of said product liquid under conditions of non-addition of alcohols.

4 Claims, No Drawings

METHOD OF SEPARATING AND RECOVERING ALKENYLBENZENES AND UNREACTED ALKYLBENZENES FROM THE ALKYLATION REACTION PRODUCT

This invention relates to a method whereby in separating and recovering alkenylbenzenes and unreacted alkylbenzenes from an alkenylation reaction product the alkenylbenzene-containing fraction and the unreacted alkylbenzene fraction suitable for recycling and reuse can be separated and recovered by distillation commercially advantageously in high purity and good yield while checking the formation of objectionable by-products whose separation from the intended alkenylbenzenes involve not only difficulty but also complicated separation operations.

The alkenylbenzene obtained by reacting an alkylbenzene with a conjugated diene of 4 – 5 carbon atoms in the presence of an alkali metal catalyst, e.g., 5-(o-tolyl)pentene-(2) obtained by reacting o-xylene with 1,3-butadiene, is a commercially valuable compound, since it can be converted to naphthalenedicarboxylic acid, a very valuable starting material for the preparation of high polymers, by effecting the latter's intramolecular cyclization reaction to convert it to 1,5-dimethyltetralin followed by dehydrogenation and oxidation.

It is known to prepare alkenylbenzenes by reacting alkylbenzenes with $C_4 - C_5$ conjugated dienes in the presence of an alkali metal catalyst (e.g., U.S. Pat. No. 3,244,758). In carrying out the foregoing alkenylation reaction continuously on a commercial scale, an excess of alkylbenzenes is used relative to the conjugated dienes for enhancing the reaction yield. Hence, in practicing this alkenylation reaction, it is usually carried out in the following manner. The alkenylbenzene-containing fraction consisting predominantly of alkenylbenzene and the unreacted alkylbenzene-containing fraction are recovered by distillation from the alkenylation reaction product, the alkenylbenzene-containing fraction being further distilled and purified, if necessary. On the other hand, the unreacted alkylbenzene-containing fraction is purified, if desired, and then recycled to the alkenylation reaction zone and reused.

In carrying out the distillation of the aforesaid alkenylation reaction product, for preventing the setting up of objectionable side reactions in this distillation step due to the presence of alkali metal catalysts and organo-alkalimetal compounds that are contained in the reaction product, an inactivation treatment of the catalysts is carried out in the aforementioned U.S. Pat. No. 3,244,758 by adding in advance isopropyl alcohol to the alkenylation reaction product.

In consequence of our researches into the matter of separating and recovering the alkenylbenzene-containing fraction and the unreacted alkylbenzene-containing fraction by carrying out the distillation under conditions of the addition of this alcohol, the following unexpected fact was discovered.

According to our researches, we found that the isopropyl alcohol added for the purpose of deactivating the catalysts was contained in the recovered unreacted alkylbenzene and that even though the amount contained was considerably small, it would greatly impair the reaction when reused in the alkenylation reaction. Thus, it is necessary to carry out a disadvantageous operation of treating the recovered unreacted alkylbenzene-containing fraction to eliminate the isopropyl alcohol. Further, not only is it difficult to remove the isopropyl alcohol to an extent as would be substantially harmless even though such a disadvantageous operation is added, but also the disadvantages involved as seen from the aspects of apparatus, operation and cost are exceedingly great in practicing this added step on a commercial scale. For example, in the instance of the alkenylation reaction of o-xylene and 1,3-butadiene in the presence of an alkali metal catalyst, it was found that there was an extreme decline in the yield of the intended 5-(o-tolyl)pentene-(2) even when the isopropyl alcohol was contained in only a small amount of 0.5 ppm in the o-xylene.

Further, in attempting the distillation and separation into an alkenylbenzene-containing fraction and an unreacted alkylbenzene-containing fraction of the alkenylation reaction product, which has substantially undergone the deactivation treatment of the catalysts with an alcohol such as isopropyl alcohol, by conveying the reaction product to the distillation zone, it was found that objectionable by-products would form during this distillation, i.e., it was found that especially in the case where it was attempted to convert the resulting alkenylbenzene into alkyltetralin by the cyclization reaction, the conversion would not proceed smoothly and, in addition, there was the formation of objectionable isomers, which were difficultly separated from the intended alkyltetralin. Whereas the olefinic double bond of alkenylbenzene, the principal product, is positioned at 2, the by-products are those isomers whose position of the double bond differs, for example, when the principal product is 5-tolylpentene-(2), the isomers are 5-tolylpentene-(1), 5-tolylpentene-(3) and 5-tolylpentene-(4). Of these isomers, that in which the olefinic double bond is in the 1-position, e.g., 5-tolylpentene-(1), can be cyclized and converted to an alkyltetralin, but in the case of the other isomers not only is it not possible to convert them to alkyltetralins, but also these other isomers react with alkyltetralins, the other product, and form high boiling products, with the consequence that the yield of the intended product declines. Furthermore, it is extremely difficult to separate and remove these objectionable isomers from the alkenylbenzenes, the intended product of the invention method, because the boiling points and chemical properties of these isomers are similar to those of alkenylbenzenes.

As a consequence of our researches with the view to overcoming the disadvantages and shortcomings such as above described, we found that by not adding the isopropyl alcohol for deactivating the catalysts but by carrying out the distillation while causing the presence in the reaction product, of the catalysts the presence of which in the distillation step was hitherto considered to be objectionable, i.e., by positively causing the presence of the catalysts, the unreacted alkali metal catalysts and organo-alkalimetal compounds, in the alkenylation reaction product during the distillation step, with the proviso that they are present in an amount adjusted to a specific range, the side reactions by which the aforesaid objectionable isomers are formed could be fully checked. Furthermore, it was found not only that the shortcoming that the reaction was impaired as a result of recycling and reusing the separated and recovered unreacted alkylbenzene could be overcome, but also that there was an improvement of the reaction yield rather than its decline. As shown by the hereinafter presented control experiments, it was found that the foregoing unexpected results could not be achieved when the amount of the catalysts deviated from the range indicated above and was either too small or too large.

It is therefore an object of this invention to provide a method whereby in separating and recovering the alkenylbenzene and unreacted alkylbenzene from the alkenylation reaction product obtained by carrying out the alkenylation reaction of an alkylbenzene and a $C_4 - C_5$ conjugated diene in the presence of an alkali metal catalyst, not only an alkenylbenzene-containing fraction can be obtained in good yield, but also an unreacted alkylbenzene fraction suitable for recycling and reuse can be obtained commercially advantageously while checking the formation of objectionable by-products whose separation from the intended alkenylbenzene not only is difficult but involves complicated separation operations as well.

Other objects and advantages of the present invention will become apparent from the following description.

According to the invention method, in carrying out the distillation and separation of the alkenylbenzene-containing fraction and unreacted alkylbenzene-containing fraction by conveying to a distillation zone an alkenylation reaction product containing an unreacted alkylbenzene, alkali metal catalysts and organo-alkalimetal compounds, the total of the concentrations of said alkali metal catalysts and organo-alkalimetal compounds is adjusted so as to be 0.09 – 15 milligram atoms, and preferably 0.12 – 8 milligram atoms, per kilogram of the product, calculated as alkali metal atoms, and the so adjusted reaction product is distilled under conditions of non-addition of an alcohol such as isopropanol to be used for deactivating the catalyst.

The method of adjusting the total of the concentrations of the alkalimetal catalysts and organo-alkalimetal compounds to an amount coming within the range specified above can be achieved by adjusting the conditions of the alkenylation reaction, the amount of the catalyst, and the amounts used of the starting alkylbenzene and conjugated diene, or by a method of mixing a suitable amount of alkylbenzene and alkenylbenzene in the reaction product. The best method is, however, that of conducting the reaction product to a catalyst separating zone and separating the product into a catalyst phase consisting predominantly of alkali metals and a hydrocarbon phase consisting predominantly of alkenylbenzene and unreacted alkylbenzene. A part of the alkali metals used as the alkenylation reaction catalyst reacts with the alkylbenzene and alkenylbenzene and become organo-alkalimetal compounds, which are contained in the reaction product. These organo-alkalimetal compounds also act as catalysts. While a part of these catalysts dissolve in hydrocarbons, a major proportion do not dissolve in hydrocarbons and are present in the form of a liquid or solid. Hence, for recovering the catalysts in a reusable state without decomposing and deactivating them, a procedure consisting of merely separating the catalyst phase from the hydrocarbon phase will do. For separating the two phases, advantageously usable are such methods as the decantation method consisting of letting the alkenylation reaction product stand still to settle the catalyst by gravity and thereafter separating and recovering the catalysts by decantation, the centrifugal method wherein the settling and separation are carried out in a centrifuge, and the method of separation by filtration. However, when considered from the standpoint of safety and the fact that the amount of catalysts to be mixed in the hydrocarbon phase can be readily controlled so as to come within the aforementioned specified range, the decantation method is preferably employed. The temperature at which the separation of the catalyst is carried out is imposed no special restrictions. In general, a higher temperature in carrying out the separation is preferred from the performance standpoint, but since side reactions tend to be set up when the temperature is too high, the separation is preferably carried out at a temperature ranging from room temperature to about 200°C., and more preferably from about 60° to about 180°C.

According to the invention method, the alkenylation reaction product to be introduced to the distillation zone is one whose concentration of alkali metal catalysts and organoalkalimetal has been adjusted as hereinabove described to a value of 0.09 – 15 milligram atoms, and preferably 0.12 – 8 milligram atoms, per kilogram of said product. This reaction product is distilled under conditions of the non-addition of alcohols for deactivating the catalysts, i.e., in the absence of isopropyl alcohol that has been used in the past for deactivating the catalysts. If the concentration of the alkali metal catalysts and organo-alkalimetal is too small, for example, as shown in the hereinafter-given control experiment, i.e., if the reaction is carried out with the addition of isopropyl alcohol, and the concentration of the alkali metal catalysts and organo-alkalimetal is made to be zero, there is such inconveniences as a decline in the effect of improving the yield of the intended product when the separated and recovered unreacted alkylbenzene is recycled and reused as the starting material for the alkenylation reaction as well as a decline in the effect of checking the formation of objectionable isomers during the distillation. On the other hand, if the concentration of the alkali metal catalysts and organo-alkalimetal exceeds 15 milligram atoms per kilogram, this also is inconvenient, as shown in the hreinafter-given control experiment, in that not only is there an increase in the amount of the by-products due to the addition reaction of the alkylbenzene, alkenylbenzene and by-products during the distillation, but also the liquid becomes viscous, with the consequence that extreme difficulty is experienced in carrying out the distillation operation.

The distillation can be carried out at either normal atmospheric, superatmospheric or reduced pressure. The use of a column top pressure of above about 50 mm Hg abs. is preferred, since the use of such a pressure serves to fully bring about the manifestation of the effects of improving the alkenylation reaction yield when reusing the recovered unreacted alkylbenzene in the alkenylation reaction. For example, in carrying out the distillation it is best to use a column top pressure ranging from 50 mm Hg abs. to 1400 mm Hg abs., and preferably 100 mm Hg abs. to 1000 mm Hg abs. As regards the distillation temperature, the distillation temperature of the unreacted alkylbenzene can be suitably chosen in accordance with the pressure used.

The distillation may be carried out either batchwise or continuously. The distillation apparatus may also be those which are known such, for example, as the tray or packed column.

The unreacted alkylbenzene that has been separated by the distillation can be recycled and reused in the aforementioned alkenylation step.

In carrying out the distillation, the separation of the alkenylbenzene-containing fraction and unreacted alkylbenzene-containing fraction can be carried out by any of the various optional modes of operation. For instance, in one mode the alkenylation reaction product can be separated into an unreacted alkylbenzene-containing fraction and an alkenylbenzene-containing fraction containing a reaction by-product fraction, following which the latter alkenylbenzene-containing fraction can be distilled further to separate same into an alkenylbenzene-containing fraction and a by-product fraction. Again, there is, for example, a mode which comprises separating the alkenylation reaction product into a fraction consisting of a mixture of an unreacted alkylbenzene-containing fraction and an alkenylbenzene-containing fraction not containing any reaction by-products and a by-product fraction, and thereafter separating the former fractional mixture into an unreacted alkylbenzene-containing fraction and an alkenylbenzene-containing fraction.

In practicing the invention method, there can be employed, for example, the following modes of operation.

1. In the method of preparing alkenylbenzenes consisting of the steps of
    A. reacting an alkylbenzene with a conjugated diene of 4 – 5 carbon atoms in the presence of alkali metal catalysts.
    B. separating the alkenylation reaction product obtained in the foregoing Step A into a catalyst phase consisting predominantly of the alkali metal and a hydrocarbon phase consisting predominantly of an alkenylbenzene and unreacted alkylbenzene,
    C. distilling the hydrocarbon phase separated in the foregoing Step B and separating same into an unreacted alkylbenzene-containing fraction and an alkenylbenzene-containing fraction, and
    D. recycling to Step A the unreacted alkylbenzene-containing fraction separated in the foregoing Step C; a method characterized by adjusting the concentration of the alkali metal catalysts and organoalkalimetal compounds contained in the hydrocarbon phase distilled in the foregoing Step C to 0.09 – 15 milligram atoms, calculated as alkali metal, per kilogram of the hydrocarbon phase.

2. In the method of preparing alkenylbenzenes consisting of the steps of
    A. reacting an alkylbenzene with a conjugated diene of 4 – 5 carbon atoms in the presence of alkali metal catalysts,
    B. separating the alkenylation reaction product obtained in the foregoing Step A into a catalyst phase consisting predominantly of the alkali metals and a hydrocarbon phase consisting predominantly of an alkenylbenzene and unreacted alkylbenzene,
    C. distilling the hydrocarbon phase separated in the foregoing Step B and separating same into an unreacted alkylbenzene-containing fraction and an alkenylbenzene-containing fraction consisting predominantly of an alkenylbenzene and reaction by-products,
    C'. distilling the alkenylbenzene-containing fraction consisting predominantly of alkenylbenzene and reaction by-products that has been separated in the aforesaid Step C, and separating same into an alkenylbenzene-containing fraction remove of by-products and a reaction by-product fraction, and
    D. recycling to Step A the unreacted alkylbenzene-containing fraction separated in the aforesaid Step C; a method characterized by adjusting the concentration of the alkali metal catalysts and organoalkalimetal compounds contained in the hydrocarbon phase used as the distillation starting material in the foregoing Step C and the alkenylbenzene-containing fraction consisting predominantly of alkenylbenzene and reaction by-products used in as the distillation starting material in the foregoing Step C' to 0.09 – 15 milligram atoms, calculated as alkali metal, per kilogram of the distillation starting material.

The process for the preparation of the alkenylation reaction product, which is obtained by reacting an alkylbenzene with a $C_4 - C_5$ conjugated diene in the presence of alkali metal catalysts, and to which the invention method finds application, is known. As the starting alkylbenzenes, mention can be made of the compounds of the following formula having at least one methyl or ethyl group substituted on the benzene ring.

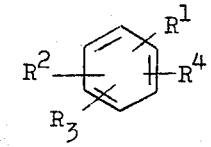

wherein $R^1$ is either methyl or ethyl, and $R^2$, $R^3$ and $R^4$ are each either hydrogen or an alkyl group of 1 – 3 carbon atoms, which may be the same or different.

Examples of the preferred alkylbenzenes includes toluene, xylene, ethylbenzene, trimethylbenzene and tetramethylbenzene, of which especially used are o-xylene, m-xylene and p-xylene, as well as the mixtures of two or more of these compounds.

On the other hand, the conjugated dienes are those of 4 – 5 carbon atoms, usable being such compounds as 1,3-butadiene and isoprene.

As catalysts for the alkenylation reaction, there can be named the alkali metals such, for example, as metallic sodium and metallic potassium. These alkali metals may be used either singly or in combinations of two or more thereof. While the amount in which the catalyst is used is imposed no special restrictions, it is preferably used in the proportions indicated below, since by using the catalyst in such proportions it becomes possible for it to demonstrate great activity even though the amount in which it is used is small. That is, the catalyst components are preferably used on the basis of 100 parts by weight of the alkylbenzene present in the reaction system in the following proportions:

1. 0.0005 – 0.005 parts by weight of metallic potassium and less than 0.1 part by weight of metallic sodium, or 2. 0.0005 – 0.085 part by weight of metallic potassium and Y part by weight as expressed by the following expression of metallic sodium:

$$0 \leq Y \leq -0.42\,Z + 0.05$$

wherein Z represents the weight of the metallic potassium per 100 parts by weight of the alkylbenzene present in the reaction system. Still more preferred is the use of the catalyst components in the proportions of 0.0005 – 0.005 part by weight of metallic potassium and Y part by weight as expressed by the following expression of metallic sodium:

$$0.0005 \leq Y \leq -0.59 Z + 0.025$$

wherein Z is as above defined. When making conjoint use of metallic potassium and metallic sodium, they may be added separately to the reaction system, but preferred is their use in the form of an alloy of the two metals.

The foregoing alkali metal catalysts can also be used supported on such carrier materials as, for example, sodium chloride, potassium chloride, calcium oxide, sodium sulfate, carbon and iron.

The aforesaid alkenylation reaction can be carried out at a temperature of preferably about 80° to about 200°C., more preferably about 100° to about 190°C., and especially preferably about 110° to about 180°C. The aforementioned conjugated dienes are used relative to the alkylbenzenes in a molar ratio of preferably 0.001 – 0.4 mole, more preferably 0.01 – 0.3 mole, and especially preferably 0.05 – 0.2 mole per mole of the alkylbenzenes. The reaction time used is preferably about 0.05 hour to about 10 hours, more preferably about 0.2 hour to about 8 hours, and especially preferably about 0.3 hour to about 4 hours.

The reaction may be carried out by the batch method in which the alkylbenzene, conjugated diene and catalyst are charged to a reaction zone followed by carrying out the reaction, or the semi-batch method in which the alkylbenzene and catalysts are first charged to a reaction zone, after which the reaction is carried out while introducing the conjugated diene, or the continuous method in which the reaction is carried out while introducing the alkylbenzene, conjugated diene and catalyst continuously to the reaction zone. Of these methods, preferred is either the semi-batch or continuous method. Particularly to be preferred is the continuous reaction method wherein a plurality of reaction zones are provided, in which zones the alkali metal catalysts are caused to be present, the alkylbenzene or a reaction mixture containing the alkylbenzene being passed through these plurality of reaction zones, while introducing the conjugated diene to at least two of such reaction zones. In this case a part or whole of the alkylbenzene may be fed to the reaction zones after mixing with the conjugated diene. If the conjugated diene and alkylbenzene are fed to the reaction zones after mixing them, this serves to prevent the conjugated diene from adhering to the vicinity of the inlet port as a result of its polymerization.

The concentration of the alkali metal catalysts and organo-alkalimetal compounds in the alkenylation reaction product, as used herein, is a value that has been quantitated and calculated in accordance with the following method of quantitation.

QUANTITATION OF ALKALI METALS

A hydrogen generating apparatus charged with 100 parts by weight of the specimen alkenylation reaction product liquid of room temperature is placed in a thermostated water tank of 25°C., after which 10 parts by weight of methanol is added to the aforesaid liquid, and the volume of the hydrogen gas generated is measured. The amount of hydrogen gas contained dissolved in the liquid is also quantitatively analyzed by means of gas chromatography. The two amounts are then added to obtain a value $(x)$. On the other hand, the amount of hydrogen gas $(y)$ contained dissolved in 100 parts by weight of the specimen alkenylation reaction product liquid before addition of methanol is also quantitated by means of gas chromatography, after which the number of milligram atoms of alkali metal is calculated by subtracting the value $(y)$ from the foregoing value $(x)$.

QUANTITATION OF THE ORGANIC ALKALI METAL COMPOUNDS

A liquid mixture of "tritium-marked water" and tetrahydrofuran is added to the specimen alkenylation reaction product liquid, after which the resulting liquid mixture is reacted with an organic metal compound. The amount of $^3$H-organic compound is then quantitated, using a liquid scintillation counter adjusted in advance by the internal standard method.

The following examples, along with control experiments, will be given for more fully illustrating several modes of practicing the method of this invention.

EXAMPLE 1

Five stirrer-equipped reaction tanks, each of 20-liter capacity (effective liquid holding capacity of 12 liters), were disposed in series, using overflow pipings to connect the several tanks. Thus, the reaction tanks were adapted to operate continuously, the liquid from the first tank flowing into the second tank via an overflow pipe, and flowing in similar manner successively through the third, fourth and fifth tanks, from which last tank the reaction product liquid is withdrawn. The hereinafter-described recovered o-xylene and dehydrated fresh o-xylene in an amount corresponding to that consumed in the reaction were fed to the first tank at a rate of 19 kg per hour. While adjusting the internal temperatures of the several tanks at 140°C. and the speed of the stirrers at 200 rpm, an alloy of metallic sodium and metallic potassium of 1:1 weight ratio was fed to the first tank at a rate of 10 grams per hour. After 4 hours had passed from the time the feed of the o-xylene and the catalyst was initiated, 0.25 kg per tank of dehydrated 1,3-butadiene was introduced to the several tanks continuously (at a rate of 1.25 kg per hour for a total of the five tanks), and the reaction of o-xylene and 1,3-butadiene was carried out.

The alkenylation reaction product liquid overflowing from the fifth tank was introduced to a cylindrical baffled decanter of inside diameter 300 mm and length 580 mm having nine baffles and of total capacity 40 liters, and the inside temperature of the decanter was adjusted to 140°C. The alkenylation reaction product liquid phase containing alkylbenzenes, alkali metal catalysts and alkali metal compounds was then withdrawn continuously from the upper part of the decanter at a rate of 20.2 kg per hour, while the catalyst phase containing predominantly the alkali metal catalysts was withdrawn from the bottom part of the decanter at a rate of 15 grams per each time at 10-minute intervals. The so obtained alkenylation reaction product liquid phase was fed continuously to the 14th plate from the bottom of an 18-plate valve tray distillation column of column diameter of 6 inches. The distillation column was operated under the conditions of an operating pressure at the top of the column of 600 mm Hg abs., a pressure at the bottom of the column of 650 mm Hg abs. and a reflux ratio of 1.0 to obtain continuously at a rate of 16.68 kg per hour a fraction containing 99.9 wt. % of unreacted o-xylene, while an alkenylbenzene-containing fraction consisting predominantly of alkenylbenzenes was withdrawn from the bottom of the column at a rate of 3.52 kg per hour. The alkenylbenzene-containing fraction obtained by distillation was then fed continuously to a column having a column diameter of 4 inches packed with Raschig rings to a height of 4 meters, where it was distilled further and separated into 5-(o-tolyl)pentenes and by-products. The distillation column was operated at a column top pressure of 500 mm Hg abs., a column bottom pressure of 530 mm Hg abs. and a reflux ratio of 2.0 to continuously obtain from the column top 5-(o-tolyl)pentene-(1) and 5-(o-tolyl)pentene-(2) of 99.8 wt. % purity at a rate of 3.06 kg per hour and from the column bottom by-products at a rate of 0.45 kg per hour. This operation was carried out continuously for 20 days. Samplings were taken from each step once daily and analyzed. From the so obtained results were calculated the concentrations and yields as 20-day average values. These results are summarized below.

1. When a part of the alkenylation reaction liquid overflowing from the fifth tank was sampled, and the concentration of 5-(o-tolyl)pentene-(1) and 5-(o-tolyl)pentene-(2) was quantitatively analyzed by the gas chromatography method, it was 15.3% and the reaction yield of 5-(o-tolyl)pentene-(1) and 5-(o-tolyl)pentene-(2) based on the 1,3-butadiene fed, was 84.0%.

2. When the metallic potassium and metallic sodium contained in the hydrocarbon liquid phase obtained from the catalyst separator were quantitatively analyzed by the hereinbefore described method of measurement from the amount of hydrogen generated, their amounts were 2.3 milligram atoms/kg. On the other hand, when the organic alkali metal compounds were quantitatively analyzed by the hereinbefore-described method and the organic sodium compounds and organic potassium compounds were calculated as sodium and potassium, the amount was 0.99 milligram atom/kg.

3. The recovery rate of the unreacted o-xylene recovered at the first distillation column was 99.7% based on the amount fed thereto of the alkenylation reaction product liquid phase, while the proportion of o-xylene converted to high boiling products or was not recovered at the distillation column was 0.2% of the alkenylation reaction product liquid phase fed thereto.

4. On analysis of the intended product obtained from the column top of the second distillation column, it was found to be 6.7 wt. % 5-(o-tolyl)pentene-(1), 93.1 wt. % 5-(o-tolyl)pentene-(2), 0.0 wt. % t-(o-tolyl)pentene-(3) and 0.2 wt. % 5-(o-tolyl)pentene-(4). Of these alkenylbenzenes, the purity of the components that could be converted to 1,5-dimethyltetralin by the cyclization reaction was 99.8%. On analysis of the by-products from the column bottom, it was found that the proportion of the 5-(o-tolyl)pentene-(2) that was isomerized or converted to high boiling components was 1.0% of the 5-(o-tolyl)pentene-(2) fed to the distillation column.

It is thus seen from the foregoing results that it was possible by operating continuously for 20 days to obtain 5-(o-tolyl)pentene-(1) and 5-(o-tolyl)pentene-(2) from the addition reaction of o-xylene and 1,3-butadiene at a stabilized yield of 82% based on the 1,3-butadiene fed and 87% based on the o-xylene fed.

EXAMPLES 2 – 4 AND CONTROL 1

The experiment was carried out exactly as in Example 1 and under identical conditions, except that the composition of the catalyst used in the alkenylation reaction and the catalyst fed to the reaction was varied. The results obtained are shown in Table 1.

Table 1

| Experiment | Example 2 | Example 3 | Example 4 | Control 1 |
|---|---|---|---|---|
| Alkenylation reaction | | | | |
| Catalyst composition: Na/K (wt. ratio) | 1 | 2 | 10 | 5 |
| Amount of catalyst fed (g/hr) | 3 | 30 | 100 | 200 |
| Reaction yield of 5-(o-tolyl)pentene-(1) and -(2) based on 1,3-butadiene fed (%) | 85 | 84 | 84 | 81 |
| Catalyst separation | | | | |
| Concentration of alkali metal atoms in the alkenylation reaction product submitted to distillation | | | | |
| Concentration of the metallic sodium and metallic potassium in the hydrocarbon liquid phase (mg atoms/kg) | 0.26 | 2.9 | 4.5 | 7.0 |
| Concentration of the organo-sodium and potassium compounds in the hydrocarbon liquid phase (mg atoms/kg) | 0.20 | 1.9 | 2.4 | 15.1 |
| Distillation | | | | |
| Recovery of o-xylene (%) | 99.8 | 99.8 | 99.7 | 98.2 |
| Concentration of products(wt.%) | | | | |
| 5-(o-tolyl)pentene-(1) | 4.8 | 7.5 | 7.6 | 8.7 |
| 5-(o-tolyl)pentene-(2) | 95.1 | 92.2 | 91.9 | 88.3 |
| 5-(o-tolyl)pentene-(3) | 0.0 | 0.0 | 0.1 | 0.6 |
| 5-(o-tolyl)pentene-(4) | 0.1 | 0.3 | 0.4 | 2.4 |
| Conversion of 5-(o-tolyl)pentene-(2) to other components (%) | 0.6 | 1.5 | 2.6 | 7.9 |
| Total yield of 5-(o-tolyl)pentene-(1) and 5-(o-tolyl)pentene-(2). (%) | | | | |
| Based on 1,3-butadiene fed | 84 | 82 | 81 | 72 |
| Based on o-xylene fed | 90 | 87 | 86 | 71 |

CONTROL 2

The alkenylation reaction was operated under exactly the same conditions as in Example 1. The alkenylation reaction product liquid overflowing from the fifth tank was fed continuously to a tank having an inside capacity of 12 liters, and a clear liquid (hydrocarbon liquid phase) was withdrawn from the top of the tank at a rate of 20.2 kg per hour, while the catalyst phase used in the reaction was withdrawn from the bottom of the tank at a rate of 75 grams per each time at hourly intervals. In this case the average residence time of the liquid in the tank was 30 minutes. The so obtained hydrocarbon liquid phase was distilled by the same method of distillation as in Example 1 to separate unreacted o-xylene, 5-(o-tolyl)pentenes and reaction byproducts. The unreacted o-xylene was recycled to the alkenylation reaction as in Example 1 and reused in the reaction. The operation was continued for 7 days in this manner. The results obtained are shown in Table 2 presented in the same form as that in the case of Example 1.

Table 2

| | |
|---|---|
| Alkenylation reaction | |
| Alkenylation reaction yield of 5-(o-tolyl)pentene-(1) and 5-(o-tolyl)pentene-(2) based on 1,3-butadiene fed (%) | 82 |
| Concentration of alkali metal atoms in the alkenylation reaction product submitted to distillation | |
| Concentration of the metallic sodium and metallic potassium in the hydrocarbon liquid phase (mg atoms/kg) | 6.3 |
| Concentration of the organo-sodium and potassium compounds in the hydrocarbon liquid phase (mg atoms/kg) | 12.1 |
| Distillation | |
| Recovery of o-xylene (%) | 98.9 |
| Concentration of products (wt. %) | |
| 5-(o-tolyl)pentene-(1) | 8.6 |
| 5-(o-tolyl)pentene-(2) | 88.8 |
| 5-(o-tolyl)pentene-(3) | 0.5 |
| 5-(o-tolyl)pentene-(4) | 2.1 |
| Conversion of 5-(o-tolyl)pentene-(2) to other components (%) | 7.5 |
| Total yield of 5-(o-tolyl)pentene-(1) and 5-(o-tolyl)pentene-(2) (%) | |
| Based on 1,3-butadiene fed | 72 |
| Based on o-xylene fed | 75 |

CONTROL 3

The alkenylation reaction was carried out under exactly the same conditions as in Example 1. The alkenylation reaction liquid overflowing from the fifth tank was continuously fed to a stirrer-equipped reaction tank of 20-liter inside capacity. On the other hand, isopropyl alcohol was fed to this tank at a rate of 150 grams per hour, and the metallic sodium, metallic potassium, and organo-sodium and potassium compounds were reacted with the isopropyl alcohol. The so obtained liquid was distilled by the same distillation procedures as used in Example 1 to separate same into o-xylene and isopropyl alcohol, 5-(o-tolyl)pentenes and reaction by-products. The o-xylene and isopropyl alcohol fraction was then continuously fed to a distillation column of 4-inch diameter packed to a height of 4 meters with Raschig rings to separate the fraction into o-xylene and isopropyl alcohol. The distillation column was operated at normal atmospheric pressure and a reflux ratio of 3.0, and the o-xylene fraction obtained from the column bottom was recycled to the alkenylation reaction step and reused. The concentration of isopropyl alcohol in the recycled o-xylene was below the identification limit (0.2 ppm). The operation was conducted in this manner for 7 days. The results obtained are shown in Table 3.

Table 3

| | |
|---|---|
| Alkenylation reaction | |
| Alkenylation reaction yield of 5-(o-tolyl)pentene-(1) and 5-(o-tolyl)pentene-(2) based on 1,3-butadiene fed (%) | 76 |
| Concentration of alkali metal atoms in the alkenylation reaction product submitted to distillation | |
| Concentration of the metallic sodium and metallic potassium in the hydrocarbon liquid phase (mg atoms/kg) | 0 |
| Concentration of the organo-sodium and potassium Compounds in the hydrocarbon liquid phase (mg atoms/kg) | 0 |
| Distillation | |
| Recovery of o-xylene (%) | 98.7 |
| Concentration of products (wt. %) | |
| 5-(o-tolyl)pentene(1) | 8.7 |
| 5-(o-tolyl)pentene-(2) | 88.0 |
| 5-(o-tolyl)pentene-(3) | 0.8 |
| 5-(o-tolyl)pentene-(4) | 2.5 |
| Conversion of 5-(o-tolyl)pentene-(2) to other components (%) | 5.5 |
| Total yield of 5-(o-tolyl)pentene-(1) and 5-(o-tolyl)pentene (2) (%) | |
| Based on 1,3-butadiene fed | 71 |
| Based on o-xylene fed | 68 |

We claim:

1. In the method wherein an alkenylation reaction product liquid obtained by the alkenylation reaction of an alkylbenzene and a $C_4 - C_5$ conjugated diene in the presence of alkali metal catalysts and containing unreacted alkylbenzene, alkali metal catalysts and organo-alkalimetal compounds is conveyed to a distillation zone at which said alkenylation reaction product liquid is separated by distillation to recover an alkenylbenzene-containing fraction and an unreacted alkylbenzene-containing fraction, the improvement which comprises adjusting the total of the concentrations of said alkali metal catalysts and organo-alkalimetal compounds in said alkenylation reaction product liquid introduced to the distillation zone so as to be 0.09 – 15 milligram atoms per kilogram of said product liquid, calculated as alkalimetal atoms, and thereafter conducting the distillation of said product liquid under conditions of non-addition of alcohols.

2. The method of claim 1 wherein said total of the concentrations of said alkalimetal catalysts and organo-alkalimetal compounds is, calculated as alkalimetal atoms, 0.12 – 8 milligram atoms per kilogram of said product liquid.

3. The method of claim 1 wherein the adjustment of the total of the concentrations of said alkali metal catalysts and organo-alkalimetal compounds is carried out by conducting said alkenylation reaction product liquid to a catalyst separating zone and separating from said product liquid a phase consisting predominantly of the catalysts.

4. The method of claim 1 wherein said unreacted alkylbenzene separated and recovered by distillation is recycled to said alkenylation reaction and reused.

* * * * *